US008677997B2

(12) United States Patent
O'Connor et al.

(10) Patent No.: US 8,677,997 B2
(45) Date of Patent: Mar. 25, 2014

(54) CHARACTERISATION OF MASK SYSTEMS

(75) Inventors: Gerard Michael O'Connor, Thornleigh (AU); John David Oates, Stanhope Gardens (AU); Peter John Deacon Wickham, Five Dock (AU); Nicola Frances Wickham, legal representative, Five Dock (AU)

(73) Assignee: ResMed Limited (AU)

(*) Notice: Subject to any disclaimer, the term of this patent is extended or adjusted under 35 U.S.C. 154(b) by 30 days.

(21) Appl. No.: 13/246,114

(22) Filed: Sep. 27, 2011

(65) Prior Publication Data
US 2012/0090610 A1 Apr. 19, 2012

Related U.S. Application Data

(63) Continuation of application No. 12/837,643, filed on Jul. 16, 2010, now Pat. No. 8,056,559, which is a continuation of application No. 10/637,771, filed on Aug. 8, 2003, now Pat. No. 7,770,579, which is a continuation-in-part of application No. 10/450,519, filed as application No. PCT/AU01/01673 on Dec. 24, 2001, now Pat. No. 7,987,847.

(60) Provisional application No. 60/258,606, filed on Dec. 29, 2000.

(51) Int. Cl.
*A61M 15/00* (2006.01)
*A61M 16/00* (2006.01)
*G01F 15/02* (2006.01)

(52) U.S. Cl.
USPC ............ 128/204.21; 128/200.24; 128/204.18; 128/204.22; 128/204.23; 128/204.26; 73/199

(58) Field of Classification Search
USPC ............. 128/204.18, 204.21, 204.22, 204.23, 128/204.26, 200.24; 73/3, 23, 199
See application file for complete search history.

(56) References Cited

U.S. PATENT DOCUMENTS

| 3,923,056 A | 12/1975 | Bingmann et al. |
| 4,554,916 A | 11/1985 | Watt |

(Continued)

FOREIGN PATENT DOCUMENTS

| WO | 99-61088 A1 | 12/1999 |
| WO | 0027457 A1 | 5/2000 |
| WO | 0037135 A1 | 6/2000 |

OTHER PUBLICATIONS

European Search Report for corresponding European Application No. 01994561.7, mailed Jul. 24, 2007, 3 pages.

(Continued)

*Primary Examiner* — Patricia Bianco
*Assistant Examiner* — Nihir Patel
(74) *Attorney, Agent, or Firm* — Lerner, David, Littenberg, Krumholz & Mentlik, LLP

(57) ABSTRACT

A method and CPAP apparatus characterizes different mask systems, e.g., masks and hoses. The CPAP apparatus can be calibrated for different mask systems and hoses by including sensors that measure flow and pressure at a flow generator of the apparatus. When the generator is fitted to a new mask system, or any changes are made to an existing one, a method calibrates the generator for the mask system. The method includes determining air flow characteristics using flow measurements from a first test period when flow through the mask system is open, measuring or estimating pressure in the mask system during a second test period when flow through the mask system is blocked and determining air flow characteristics of the diffuser of the mask system using the air flow characteristics of the air delivery hose determined during the first period and the pressure measurements made during the second period.

12 Claims, 7 Drawing Sheets

(56) References Cited

U.S. PATENT DOCUMENTS

| | | |
|---|---|---|
| 4,944,310 A | 7/1990 | Sullivan |
| 5,245,995 A | 9/1993 | Sullivan et al. |
| 5,551,419 A | 9/1996 | Froehlich et al. |
| 5,645,053 A | 7/1997 | Remmers et al. |
| 6,257,234 B1 | 7/2001 | Sun |
| 6,279,569 B1 * | 8/2001 | Berthon-Jones ......... 128/200.24 |
| 6,484,719 B1 * | 11/2002 | Berthon-Jones ......... 128/204.23 |
| 6,635,021 B1 | 10/2003 | Sullivan et al. |
| 7,770,579 B2 | 8/2010 | O'Connor et al. |

OTHER PUBLICATIONS

International Preliminary Examination Report for PCT/AU01/01673 dated May 17, 2002.

International Search Report for PCT/AU01/01673 dated Mar. 1, 2002.

* cited by examiner

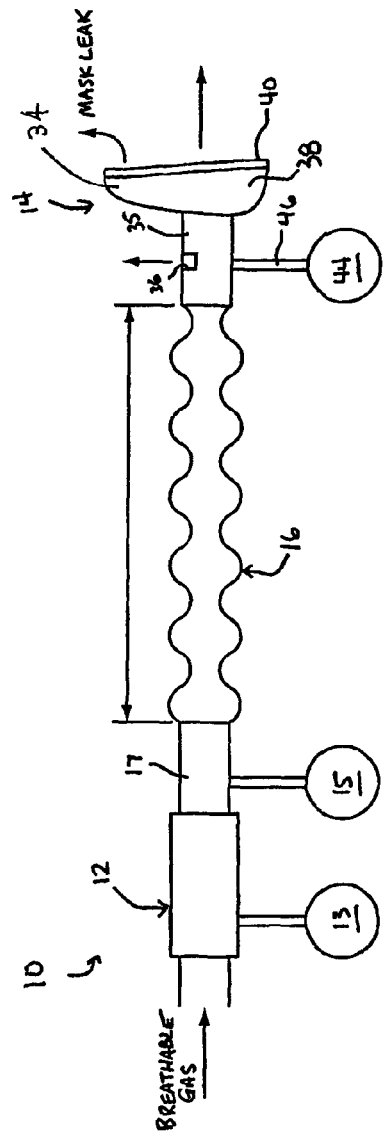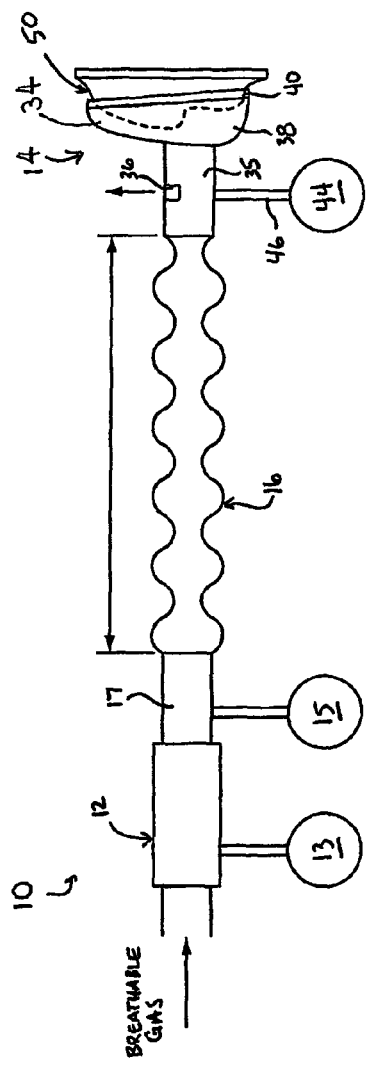

CHARACTERISATION OF MASK SYSTEMS

CROSS-REFERENCE TO RELATED APPLICATIONS

This application is a continuation of U.S. patent application Ser. No. 12/837,643, filed Jul. 16, 2010, now U.S. Pat. No. 8,056,559, which is a continuation of U.S. patent application Ser. No. 10/637,771, filed on Aug. 8, 2003, now U.S. Pat. No. 7,770,579 which is a continuation-in-part of U.S. patent application Ser. No. 10/450,519, filed on Jun. 16, 2003, now U.S. Pat. No. 7,987,847 which is a national stage application of PCT application no. PCT/AU01/01673, filed Dec. 24, 2001, which claims priority from U.S. Provisional application Ser. No. 60/258,606, filed on Dec. 29, 2000. The contents of all of these applications are incorporated by reference in their entireties.

FIELD OF THE INVENTION

The invention generally relates to a method and an apparatus for characterizing mask systems used in treatment of sleep disordered breathing (SDB). More specifically, the invention relates to a method and apparatus for use with different mask systems that can determine air flow characteristics of the different mask systems.

BACKGROUND OF THE INVENTION

The use of nasal Continuous Positive Airway Pressure (CPAP) for the treatment of Obstructive Sleep Apnea (OSA) was taught by Sullivan and described in U.S. Pat. No. 4,944, 310, which is entitled "Device for Treating Snoring Sickness". The treatment generally provides a supply of air to a patient's upper airways at pressures, typically in the range of 4 to 20 cm $H_2O$, which acts to "splint" open the patient's airways. Typically, the CPAP apparatus includes (i) a blower for providing a source of pressurised breathable air to a patient, (ii) a patient interface to be removably worn by the patient, and (iii) an air delivery hose for transferring the pressurised breathable air from the blower to the patient interface. The blower typically includes an electric motor and impeller. One end of the air delivery hose or conduit is connected to the output of the blower and the other end is connected to the patient interface.

Some devices for treating SDB or assisting ventilation provide two pressure levels, one during patient inhalation and a different pressure during patient exhalation. The switching between two pressures may be triggered by a timer, a pressure sensor, a flow sensor, a volume sensor or some combination using techniques well known in the ventilator arts.

An automatically adjusting method and device was first described by Sullivan and Lynch in U.S. Pat. No. 5,245,995, which describes a pressure transducer that, in addition to detecting snoring sounds, can detect other respiratory parameters such as the rate of breathing, inhaled air flow volume and inhaled air flow rate. The device also included a feedback system controlling the output pressure of the air source so as to increase the output pressure in response to the detection of snoring or abnormal breathing patterns, and reduce the pressure in the absence of such patterns. The use of such a device can lead to improved patient comfort since patients receive lower pressures during the portion of their sleep when there are no indications of OSA, but higher pressures when they are needed. Examples of devices operating in this manner are the AutoSet® brand of nasal CPAP devices manufactured by ResMed Limited, Australia.

Other conditions may be treated by nasal ventilation such as Cheyne-Stokes breathing, as described in International Patent Application WO 99/61088. Such devices require very accurate measurement of flow and pressure. OSA is an example of a broader class of disorders generally referred to as sleep disordered breathing (SDB). In this specification, a reference to apparatus for the treatment of OSA is intended to include a reference to apparatus for treating SDB. Nasal CPAP apparatus for treating SDB from a special subgroup within the broader group of mechanical ventilators. Whilst mechanical ventilators are often closed systems with respect to airflow, the blower, conduit and patient interface system used for the treatment of sleep disordered breathing is typically an open system with respect to airflow. That is, the system for treating SDB typically includes a deliberate air leak. A deliberate leak is to be contrasted with unintentional leak. The patient interface in a system for treating SDB typically includes a diffuser which produces a deliberate air leak which, amongst other things, reduces rebreathing of exhaled air. In addition as in most systems, there exists the potential for unintentional leak flow. For example, if the mask is not correctly positioned on the face, or unsuitable for a particular face, there may be leak around the periphery of the face contacting portion of the mask. In some applications of SDB treatment, for example to assist in correctly synchronizing the blower flow with spontaneous patient respiratory effort, it is important to measure accurately the leak, both deliberate and unintentional, from the system.

The "black box" which incorporates the blower, switches, power supply and control circuitry is sometimes termed a "flow generator". Alternatively, a source of high pressure air may be connected to a controllable valve arrangement to provide air at the required pressure and flow rates. All of these systems may be described as controllable sources of breathable gas.

In most modern devices for treating SDB, especially those providing sophisticated therapies, there is a need for the device to be able to measure accurately the pressure in the patient interface and the flow of air to the patient. One way this can be accomplished is to place flow and pressure sensors directly in the patient interface (such as a mask). Another way this can be accomplished is to place the flow and pressure sensors in the flow generator and have a sense tube connected from the flow generator to the patient interface.

Whilst accurate measurements of, for example, pressure and flow can be made directly at a mask, such an arrangement can be inconvenient from a patient's point of view since it may require additional sensing tubes to be carried from the flow generator to the patient interface. Sense tubes can be difficult to assemble, difficult to clean and may become tangled during use. Alternatively, if the characteristics of the conduit and patient interface are known, it is possible to estimate the desired variables, such as pressure and flow, in the mask using measurements in the flow generator.

Hence there is a need for a way to measure the characteristics of the conduit and patient interface. In this way, the sophisticated apparatus for treating SDB can measure accurately the mask pressure without requiring sense tubes to be connected between the flow generator and the mask.

A large variety of mask systems are today available and each has different characteristics, such as different pressure drop along the conduit and diffuser flow. Furthermore, the characteristics of different samples of a given mask system can vary due to variation during manufacturing. In order that a given flow generator be able to work with a range of mask systems, each mask system must be characterized by the manufacturer for use with the flow generator and the characteristics may be stored in the flow generator, for example, or in some other recordable medium device. In the event that new mask systems are developed, the flow generator may need to be returned to the manufacturer to be tested with the new mask system.

The flow generator then generates a flow and pressure model of this particular hose and mask system and uses these parameters to calculate hose pressure drop, diffuser flow and mask leak as part of its normal operation. The procedure is prompted on the LCD display with checks to make sure the operator is doing the right thing. The characterization procedure takes less than 1 minute.

There is a need for a method and apparatus which enables the characteristics of a wide range of patient interfaces and conduits to be determined without requiring that a flow generator be returned to the manufacturer.

SUMMARY OF THE INVENTION

One aspect of the invention is to overcome the short comings of the prior art. Another aspect is to provide a breathing assistance apparatus, e.g., a CPAP apparatus, that can be used with a variety of mask systems having different pressure and/or flow characteristics.

According to one preferred embodiment of the present invention, there is provided a method for determining air flow characteristics of a mask system connected to CPAP apparatus comprising a flow generator, the mask system including an air delivery hose and a patient interface including a diffuser, the flow generator including a controllable air blower, a flow sensor and a pressure sensor. The method includes determining air flow characteristics of the air delivery hose using flow measurements made during a first test period when the flow through the patient interface is open; measuring pressure in the patient interface during a second test period when the flow through the patient interface is blocked; and determining air flow characteristics of the diffuser using the air flow characteristics of the air delivery hose determined during the first test period and the pressure measurements made during the second test period.

In accordance with an embodiment of the invention, the mask system is characterised to determine the pressure drop along the conduit as a function of blower, flow rate. In accordance with an embodiment of the invention, the pressure drop across the diffuser is determined as a function of mask pressure.

According to another embodiment of the invention, a method is provided for determining air flow characteristics of an air delivery hose connected to a flow generator in a CPAP apparatus, the flow generator including a controllable air blower, a flow sensor and a pressure sensor. The method comprises measuring an air flow rate through the controllable air blower during a test period; and determining air flow characteristics of the air delivery hose using the flow rate measurements made during the test period.

According to another embodiment, a method is provided for determining air flow characteristics of a mask system connected to a controllable source of breathable gas, the mask system including an air delivery hose and a patient interface. The method comprises measuring an air flow rate at the controllable source of breathable gas during a controlled pressure test period when the mask system is open; measuring a pressure at the controllable source of breathable gas during a controlled flow test period when the mask system is blocked; and determining air flow characteristics of the mask system based on the measured pressure and the measured air flow rate made during the controlled pressure test period and the controlled flow test period, respectively.

In still another embodiment, a CPAP apparatus useful in treatment of a patient includes a housing; a respiratory mask system in communication with the housing, the respiratory mask system comprising an air delivery hose and a patient interface including a diffuser; a flow generator configured to deliver a supply of breathable gas to the patient and being associated with the housing, the flow generator being controllable to supply a controllable source of breathable gas to the patient interface through the air delivery hose during a test period, wherein a plurality of flow measurements of the controllable source of breathable gas are made during the test period; and a processor configured to determine a plurality of air flow characteristics of the respiratory mask system at least based on the plurality of flow measurements made during the test period.

Another embodiment-encompasses a machine readable medium containing machine executable instructions for carrying out the method according to the claims.

In still another embodiment, a CPAP apparatus useful in treatment of a patient, the CPAP apparatus comprises a housing; a respiratory mask system in communication with the housing, the respiratory mask system comprising an air delivery hose and a patient interface including a diffuser orifice; a flow generator configured to deliver a supply of breathable gas to the patient and being associated with the housing, the flow generator being controllable to supply a controllable source of breathable gas to the patient interface through the air delivery pose during a test period, wherein a plurality of flow measurements of the controllable source of breathable gas are made during the test period; means for determining air flow characteristics of the air delivery hose using flow measurements made during a first portion of the test period when the flow through the patient interface is open; means for measuring pressure in the patient interface during a second portion of the test period when the flow through the patient interface is blocked; and means for determining air flow characteristics of the orifice using the air flow characteristics of the air delivery hose determined during the first portion of the test period and the pressure measurements made during a second portion of the test period.

In yet another embodiment, a CPAP apparatus for use with a respiratory mask system comprising an air delivery hose and a patient interface including a diffuser, comprises a housing; a flow generator configured to deliver a supply of breathable gas to the patient and being associated with the housing, the flow generator being controllable to supply a controllable source of breathable gas to the patient interface through the air delivery hose during a test period, wherein a plurality of flow measurements of the controllable source of breathable gas are made during the test period; and a processor configured to determine a plurality of air flow characteristics of the respiratory mask system at least based on the plurality of flow measurements made during the test period. A respiratory mask system for use with this CPAP apparatus is also envisioned.

Also, a method is provided for calibrating a flow generator in a CPAP apparatus for use with a mask system including a diffuser and an air delivery hose connecting the flow generator and the mask system. The method comprises providing the flow generator with two different air flows, representative of a pressure drop in the air delivery hose when flow through the mask system is open; providing the mask system with two different pressures, representative of a flow of the diffuser and other leaks out of the mask system; and blocking flow through the mask system while providing the mask system with the two different pressures.

In accordance with an embodiment of the invention, in apparatus including a blower and a conduit, with the conduit connected to the blower outlet, a flow sensor for measuring the flow of air at the blower outlet and a pressure sensor for measuring the air pressure at the blower outlet, there is provided a method for estimating the pressure drop along the conduit for a range of blower flow rates by modelling the pressure drop along the conduit as a quadratic function of flow with two parameters, and determining the two parameters by conducting two tests: (i) a first test in which the blower is operated at a first flow rate and develops a first blower outlet pressure; and (ii) a second test in which the blower is operated at a second flow rate and develops a second blower outlet pressure.

In accordance with an embodiment of the invention, in apparatus including a blower and a conduit, with the conduit connected to the blower outlet, a flow sensor for measuring the flow of air at the blower outlet, a pressure sensor for measuring the air pressure at the blower outlet, and a mask including a diffuser, the diffuser having a diffuser flow, there is provided a method for estimating the pressure drop across the diffuser for a range of blower flow rates by modelling the pressure drop across the diffuser as a quadratic function of mask pressure and blower flow. Although certain embodiments of the invention are illustrated and described herein as having certain features, one skilled in the art would recognize that alternative embodiments of the invention could be provided based on at least one or more features, either individually or in combination, of the illustrated and described embodiments.

One embodiment of the invention includes a method for automatically determining flow characteristics of a patient interface comprising the steps of providing a positive airway pressure treatment apparatus with a patient interface. A plurality of flow levels is delivered in a predetermined test range through the patient interface while the patient interface is unblocked and disengaged from a patient in a manner that will not apply pressure to the airway of the patient while pressure is measured at a remote location from the patient interface. In the method an impedance table is generated from measured values of pressure and flow that are associated with each of the plurality of flow levels in the predetermined test range. The flow characteristic of the patient interface is then determined from the impedance table during the provision of positive airway pressure treatment to a patient. In the preferred embodiment, the delivering of flow progresses from a predetermined flow level at a lower end of the test range and continually increases to additional flow levels until reaching a predetermined flow level at an upper end of the test range. The successive flow levels of the plurality of flow levels may be separated by approximately equally spaced intervals or common flow intervals.

In the preferred embodiment, flow characteristics may be determined from the table directly or through a linear interpolation operation. In addition, the pressure at a mask portion of the patient interface may be monitored to ensure that the mask pressure remains approximately at ambient during the step of delivering. Optionally, safety procedures for aborting use of the generated table may be implemented based on conditions including (a) if the mask pressure exceeds a threshold value or does not remain approximately at ambient pressure; (b) if a predetermined flow level of the test range is not delivered in the step of delivering; or (c) if a determined impedance value exceeds by a threshold value a predetermined maximum impedance for the patient interface. With the table, the pressure in the patient interface may be estimated by reducing a measured pressure taken at the remote location by a pressure drop determined from the impedance table at a measured flow.

BRIEF DESCRIPTION OF THE DRAWINGS

The benefits of the present invention will be readily appreciated and understood from consideration of the following detailed description of embodiments of this invention, when taken with the accompanying drawings, wherein:

FIG. 2 is a schematic diagram of the CPAP apparatus shown in FIG. 1, wherein air flow to the patient is open;

FIG. 3 is a schematic diagram of the CPAP apparatus shown in FIG. 1, wherein air flow to the patient is blocked;

DETAILED DESCRIPTION OF THE PREFERRED EMBODIMENTS

Figure 1:
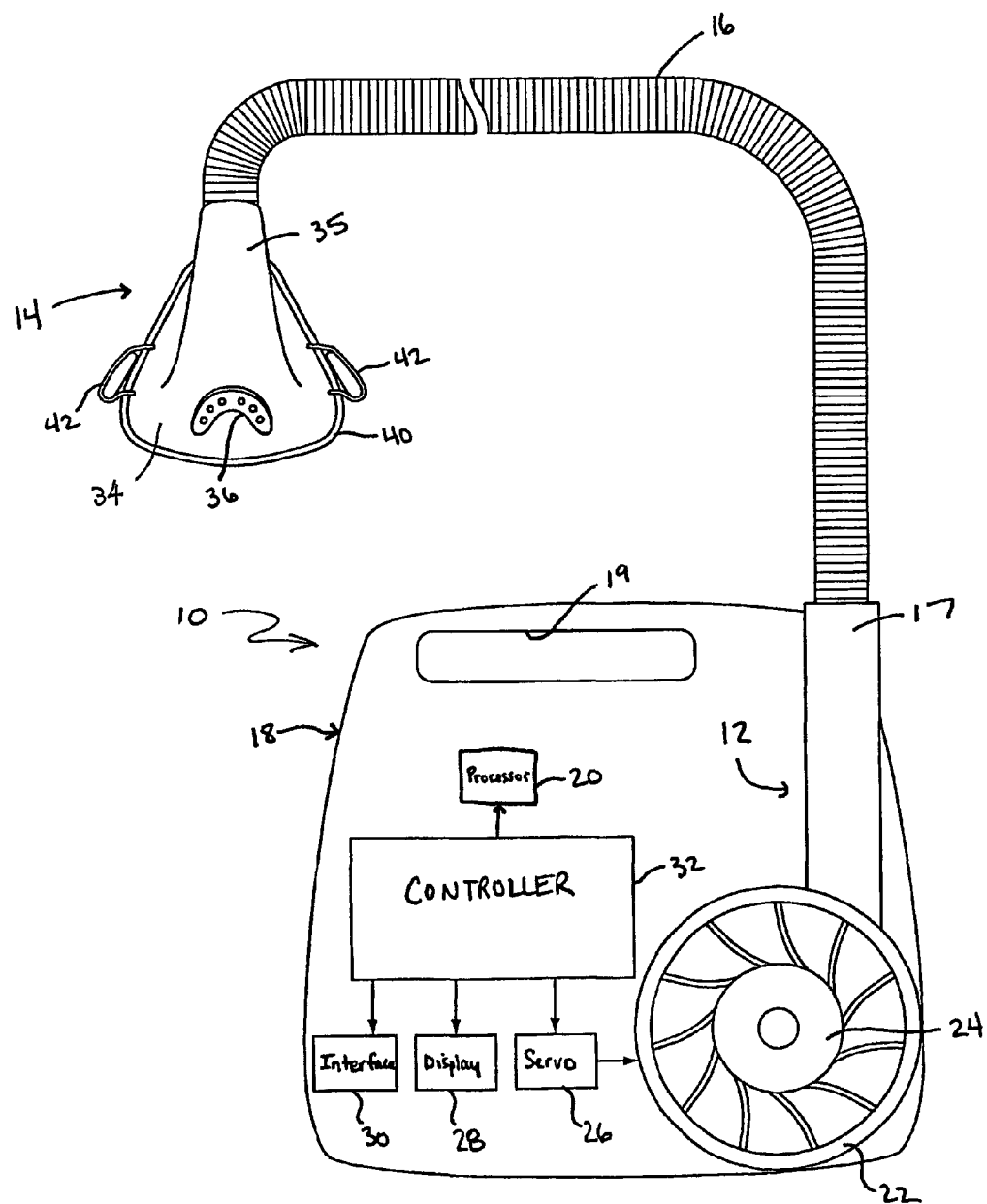
FIG. 1 is a illustrative diagram showing a CPAP apparatus in accordance with the principles of the present invention.

FIGS. 1-3 show a CPAP apparatus for treating a patient in accordance with the principles of the present invention. In the illustrated embodiment, the CPAP apparatus, generally indicated at 10, comprises a controllable air blower or flow generator 12 that is in communication with a respiratory mask system, generally indicated at 14. The respiratory mask system 14 includes an air delivery hose 16 that connects the respiratory mask system 14 to the flow generator 12 to supply breathable gas through the respiratory mask system 14 to the patient. The flow generator 12 is configured to deliver a supply of breathable gas to the patient at a specific flow rate and pressure, for example. As shown in FIGS. 2 and 3, the flow generator 12 includes a flow sensor 13 and a pressure sensor 15, to measure flow rate and pressure respectively, at an output 17 of the flow generator 12. The output 17 is preferably connected to the air delivery hose 16.

The flow generator 12 is configured to supply a controllable source of breathable gas, such as oxygen, to the mask system 14 through the air delivery hose 16 during a test period, which will be described in greater detail below. A plurality of flow measurements, for example, flow rate and pressure, of the controllable source of breathable gas are made during the test period at the output 17 of the flow generator 12.

The flow generator 12 is capable of delivering the source of breathable gas at a flow up to about 100 L/min, for example, at low pressures, ranging from about 0.25 to about 2 cm $H_2O$, smoothly and accurately. If necessary, the flow generator may also be configured to provide higher flow and pressure.

As best shown in FIG. 1, the flow generator 12 can be provided within the housing 18, which can be made from a sufficiently resilient material, such as plastic or metal. Alternatively, the flow generator 12 can be provided remote from the housing 18.

The housing 18 may include an opening or slot 19 formed in the exterior thereof, which may be used as a handle to transport the CPAP apparatus 10. The resilient structure of the housing 18 can substantially help support and protect a processor 20, an impeller 22, a motor 24, a servo-control circuit 26, a display 28, a user interface 30 and a controller 32. The controller 32 may be configured to control the operation of one or more of the processor 20, the impeller 22, the motor 24, the servo-control circuit 26, the display 28, and the user interface 30, as is generally known. The controller or processor includes integrated chips, a memory and/or other instruction or data storage medium to implement the methodologies described in more detail herein. Programmed instructions or machine control instructions are either coded on integrated chips in the memory of the device or may be loaded as software.

As seen in FIG. 1, the user interface 30 and the display 28 are provided in the housing 18 of the CPAP apparatus 10 and are configured to control and manipulate various functions that may be available to the particular CPAP apparatus 10. The user interface 30 may be in the form of a barcode, a keyboard, a mouse, a touch screen, a remote terminal or a voice activation system, for example, to accept input from a user, such as a patient or doctor, for example. The display 28 may be a touch screen display or an LCD display and may be configured to display various parameters, such as, for example, air flow characteristics of the air delivery hose 16 or mask system 14, the flow rate measured by the flow sensor 13 and the pressure measured by the pressure sensor 15. The display 28 can be configured to display delivered flow (by the flow generator 12) with a prompt so that a user or patient can minimize delivered flow before making air flow characteristic measurements.

The motor 24 is coupled to the impeller 22 to drive the impeller 22. When driven, the impeller 22 generates a source of breathable gas, which can be supplied through the air delivery hose 16 to the, mask system 14.

The processor 20 is configured and arranged to determine a plurality of air flow characteristics of the respiratory mask system 14 using a plurality of flow measurements made during the test period. These air flow characteristics could be displayed on the display 28, for example.

Additionally, the processor 20 may be capable of performing various calculations to a specific accuracy, for example, 32 bit floating point. The processor 20 may be configured and arranged to perform calculations at any other accuracy as well, which could depend on the desired calculation and application, for example. The servo-control circuit 26 cooperates with the processor 20 and the flow generator 12 to allow for the maintenance of a pressure in the mask system 14, for example, within strictly defined error limits.

Table 1, as shown below, models a preferred minimum accuracy and a preferred optimal accuracy for various system parameters, such as delivered flow accuracy, stability and linearity and delivered pressure accuracy and stability.

TABLE 1

| Parameter | Minimum Accuracy | Optimal Accuracy |
| --- | --- | --- |
| Delivered flow accuracy | +/−3L/min (same as mask leak requirement) | +/−1.5 L/min (½ mask leak requirement) |
| Delivered flow stability | Same as mask leak requirement over any period of use | ½ A mask leak requirement over any period of use |
| Delivered flow linearity | <5% deviation from straight line (Fig. 5) | <2% deviation from straight line (Fig. 5) |

TABLE 1-continued

| Parameter | Minimum Accuracy | Optimal Accuracy |
| --- | --- | --- |
| Delivered pressure accuracy | +/−0.5 cmH$_2$O at 20 cmH$_2$O | +/−0.25 cmH$_2$O at 20 cmH$_2$O |
| Delivered pressure stability | +/−0.5 cmH$_2$O over any period of use | +/−0.25 cmH$_2$O over any period of use |

As shown in FIGS. 1-3, the air delivery hose 16 may be any conventional hose. However, in some applications, such as in some hospital and clinical situations with acute or sick patients, different requirements may be needed for the hose system 16. In particular it is likely that an antibacterial filter with ongoing maintenance would be beneficial in those situations.

In this situation, an abbreviated calibration of the hose, which will be described in greater detail below, may be done automatically or manually every time the mask is disconnected from the patient. This system could also track use of antibacterial filters and warn when they are getting clogged and need to be changed.

The mask system 14 is connected to an air supply source provided by the flow generator 12 by the air delivery hose 16. The mask system 14 may be integrally attached to the air delivery hose 16 or may be connected thereto with fasteners, such as clamps, for replacement or interchangeability of the mask system 14. The air supply source may deliver unregulated air to the mask system 14, because the pressure sensor 15 associated with the flow generator 12 maybe configured to determine the required pressure of the air needed by the patient by the relative strength of the patient's breaths.

The mask system 14 includes a patient interface or mask 34 and an elongated projecting portion 35, which maybe connected to the air delivery hose 16. A diffuser 36, in the form of an orifice, is formed in the elongated projecting portion 35 and diffuses air exhaled by the patient. Other masks may be used with apparatus according to an embodiment of the invention. For example, apparatus in accordance with the invention may be used to determine the flow characteristics of a mask system such as the MIRAGE™ mask, the ULTRA MIRAGE™ mask, the BUBBLE™ mask or the MODULAR™ mask, all of which are manufactured by ResMed Limited, Australia.

The patient interface 34 may be anyone of a number of different patient interfaces, such as a nasal mask, a nose and mouth mask, a full-face mask, nasal prongs (or cannulae) and nasal pillows. Generally, the patient interface 34 includes some form of mask retaining feature, such as headgear, to position the mask system 14 on the patient's face and to counterbalance the force which results from the application of pressurized air which seeks to push the mask 34 or mask system 14 off the patient's face.

The diffuser 36 can be passive or semi-active, e.g., the diffuser 36 could be an opening, a plurality of openings, or an opening or openings that are partially covered, grated etc., that allow air to pass through.

The mask 34 is shown as a nasal mask and has a generally triangularly-shaped chamber 38 constructed from a relatively rigid material, such as polycarbonate, with an open side which, when in use, is positioned against the patient's face. The edge of the open side, i.e., a face-contacting portion 40, helps form a seal on the patient's face. The face-contacting portion 40 is typically soft to assist with patient comfort and may be made from foam, rubber or polystyrene, for example.

A good seal should be provided between the patient's face and the face contacting portion 40, with few leaks because leaks can cause air jetting and noise, which may be uncomfortable for the patient. Thus, mask 34 includes a number of headgear-receiving portions 42 extending from opposite sides thereof to receive straps or other portions of the headgear, for example. Patient comfort is important and should be considered when selecting the type of mask 34 since the patient may be sleeping or resting while wearing the mask 34.

In accordance with one embodiment of the invention, the pressure in the patient interface can be estimated once the conduit characteristics have been determined. In such an embodiment it is only necessary to determine the pressure at the blower outlet and the flow at the blower outlet in order to estimate the pressure in the patient interface, in conjunction with known conduit characteristics. Hence such an embodiment does not require a pressure transducer in the patient interface, or to be connected to the patient interface via a sense tube. Furthermore, such an embodiment of the invention can be used in conjunction with a wide variety of commercially available masks which do not include pressure transducers in the mask, or pressure sense tubes in the mask.

The pressure delivered to the entrance of the patient's airways can also be measured directly in the patient interface 34. In this case, a pressure sensor 44, for example, a pressure transducer, may be mounted on or near the patient interface 34 and in communication with the interior chamber 38 or the projecting portion 35 of the mask 34 by way of a port or linking sensing tube 46. Alternatively, a sensing tube can be connected between an appropriate port on the patient interface 34 and a pressure sensor (not shown) located remotely from the patient interface 34, such as in the air blower housing 18.

In an alternative embodiment, although not shown, the CPAP apparatus can include an under or over pressure alarm coupled to a pressure tube extending from the mask 34 for accurate measurements of mask pressure.

This configuration may generally be best suited to provide variable pressure regimes. The under or over pressure alarm can measure pressure at the flow generator 12 to allow the maintenance of a continuous accurate model of the hose pressure drop and so allows the alarm system to measure pressure at the flow generator 12.

Characteristics for common masks and hose systems could be stored in the flow generator or a removable storage medium. Alternatively, those common characteristics could be manually entered via keyboard or barcode. Thus, the CPAP apparatus 10 may include a slot, for example, that is configured to allow a removable storage medium to be inserted into the slot for storing collected data or characteristics for common masks and hose systems. The slot could be conveniently located anywhere on the CPAP apparatus, but should be located so minimal effort is required to insert and remove the storage medium from the CPAP apparatus 10.

The removable storage medium could be a magnetic or flash type of storage, which is commonly compatible with personal computers, handheld devices, cameras, and printers and is capable of storing hundreds of megabytes of data at a minimum. Additionally; the removable storage medium could contain information about the mask system 14 or may include other parameters provided by a physician, for example. In this case the removable storage medium would have read from and write to capabilities and information that was imparted to the removable storage medium by the patient or the physician could be utilized by the CPAP apparatus 10 to control certain parameters. For example, different masks have different flow characteristics, it would be beneficial to impart information about the mask onto the removable storage medium so the CPAP apparatus could vary the provided air pressures or flow rates accordingly. In this case, it would be inexpensive for the patient to change masks because the mask information and characteristics could easily be changed to accommodate different masks, for example. Data for each particular mask can be provided by the mask manufacturer and when the patient purchases the mask, he or she could simply insert the card into the CPAP apparatus 10 and the apparatus could reconfigure itself accordingly.

In the CPAP apparatus 10, the flow generator 12 may be preset to operate within a given speed range giving coarse control of the pressure which is delivered to the patient through the air delivery hose 16. However, the actual pressure at the patient interface will vary throughout the respiratory cycle. For instance, as the patient or other user inhales, the pressure measured at the patient interface increases while during exhalation the measured pressure decreases. The average air flow to the patient is assumed to be zero, as the air supplied to the patient is effectively balanced by air exhaled by the patient.

The pressure delivered to the entrance of the patient's airways can be estimated by measuring the pressure at the output 17 of the flow generator 12 and applying a correction factor in accordance with the known characteristics of the relevant conduit and patient interface, as will be described in greater detail below.

In most mask systems, there exists the potential for leak flow. For example, if the mask is not correctly positioned on the face, or unsuitable for a particular face, there may be leak around the periphery of the face-contacting portion of the mask. In some applications, it is important to measure accurately the leak from the system, for example in a spontaneously breathing patient, to assist in correctly synchronizing the air flow from the flow generator 12 with patient respiratory effort.

The accuracy of the flow and pressure measurements, as shown in Table 1, has a direct effect on the accuracy of a derived mask leak. However this accuracy will not effect the accuracy of a zero point of mask leak. Any zero drift in the measurements will effect both the scale and zero of mask leak.

A model showing the mask components (e.g., hose pressure drop, mask diffuser flow, and any other leaks) as quadratic expressions of pressure drop in regard to flow can be represented by the following quadratic expression:

$$\text{Pressure Drop} = A*\text{Flow} + B*\text{Flow}^2$$

The term A is attributed to friction losses, which are proportional to flow, and the term B is based on the Bernoulli equation where pressure drop is proportional to flow squared ($\text{Flow}^2$).

To obtain a more accurate measurement of mask leak, a flow blocking member 50 (FIG. 3) can be provided to block portions of the patient interface 34 and the projecting portion 35 so that flow through the mask system 14 is blocked. To ensure a proper fit, a shape of the flow blocking member 50 is complementary to a shape of the patient interface 34. Also, the shape of the flow blocking member 50 may be representative of a human nose, a human face or a partial human face. The flow blocking member 50 may be shaped such that it can serve to block flow in a number of masks having different configurations. The flow blocking member 50 may be affixed to the flow generator 12 so that it does not become lost and remains easily accessible to the patient, or the flow blocking member 50 can be free from attachment to the flow generator 12.

Figure 4:
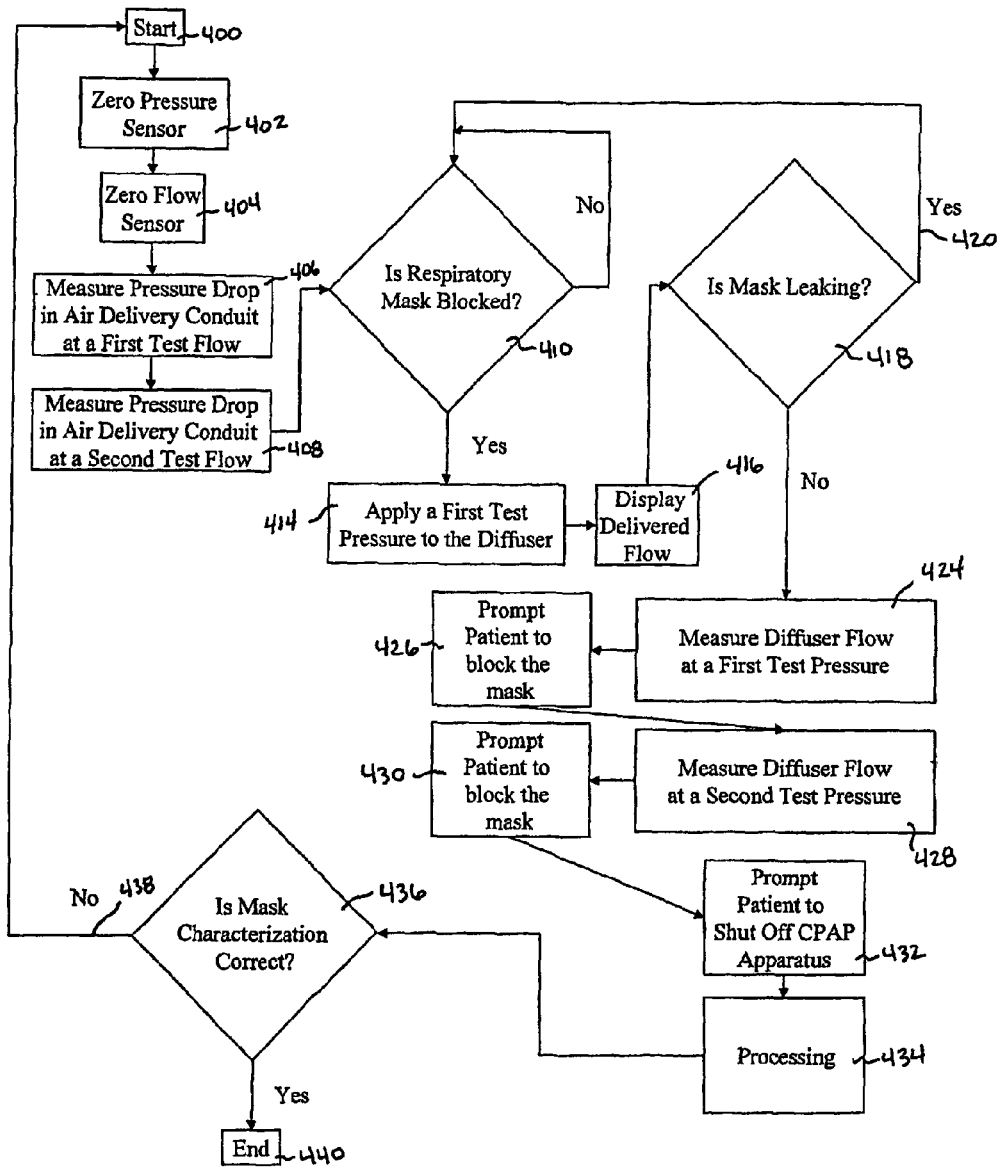
FIG. 4 is an illustrative diagram showing a method in accordance with the principles of the present invention.

Reference will now be made to FIG. 4, in which a method for characterizing different mask systems in accordance with the principles of the invention. The method can model various characteristics of mask components, such as pressure drop in the hose 16, mask diffuser 36 flow and any other leaks in the mask system 14. In FIG. 4, a flow chart is used to represent the method for characterizing different mask systems according to the principles of the present invention. At 400, the method begins. At 402, the pressure sensor 15 associated with the flow generator 12 is zeroed, and at 404, the flow sensor 13 associated with the flow generator 12 is zeroed. During data collection, the delivered flow, as measured by the flow sensor 13, and the delivered pressure, as measured by the pressure sensor 15, should be kept as constant as possible.

At 406, a pressure drop in the air delivery hose 16 is measured at a first test flow rate. At 408, a pressure drop in the air delivery hose 16 is measured at a second test flow rate. The quadratic expression having constants Hose A and Hose B can be used to determine or calculate air flow characteristics of the air delivery hose 16. The quadratic expressions are represented as follows:

Hose $A=(yX^2-xY^2)/(xX^2-Xx^2)$ and

Hose $B=(xY-yX)/(xX^2-x^2X)$

Figure 5:
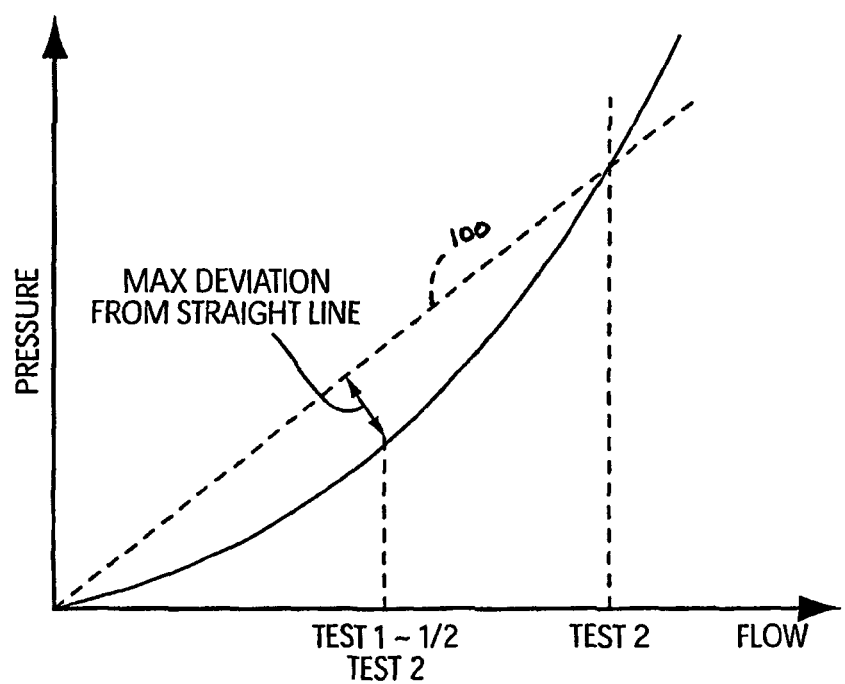
FIG. 5 is an illustrative diagram showing pressure plotted versus flow for the CPAP apparatus shown in FIG. 1.

The pressure drops in the air delivery hose 16 at the first and second flow rates are represented as y and Y, respectively. Leaks in the diffuser 36 at a lower flow rate and at a higher flow rate are represented as x and X, respectively. It should be noted that the positive quadratic nature of the typical pressure/flow characteristic of these components, the first and second flow rates (or pressures) provide substantially better resolution with one at a high value and the other at half of the high value. This relationship is shown in FIG. 5, wherein test 1 is a flow rate having half the value of "test 2, which is a flow rate having a high value. In FIG. 5, a maximum linear deviation from the straight line 100 (about 5%) is shown corresponding to flow rate represented by test 1, which is the value equal to half of the high value.

The mask calibration procedure produces the following measurements, as shown in Table 2, which are analyzed to produce the A and B coefficients for the mask system model described above:

TABLE 2

| Name | Parameter | Example value |
| --- | --- | --- |
| HoseTF1 | Lower test flow for hose | 40 L/min |
| HoseTP1 | Pressure drop down hose at lower test flow | 0.1 to 0.4 cmH2O |
| HoseTF2 | Upper test flow for hose | 80 to 100 L/min |
| HoseTP2 | Pressure drop down hose at upper test flow | 1 to 4 cmH$_2$O |
| DiffTP1 | Lower diffuser test pressure | 6 cmH$_2$O |
| DiffTF1 | Flow at lower diffuser test pressure | 10 to 20 L/min |
| DiffTP2 | Upper diffuser test pressure | 12 cmH2O |
| DiffTF2 | Flow at upper diffuser test pressure | 15 to 40 L/min |

The values shown in Table 2 are examples only and are not limiting, rather they are provided for understanding only.

The true test pressures (TrueDiffTP1, TrueDiffDP2) for the diffuser can be calculated using HoseA and HoseB using the following equations:

TrueDiffTP1=DiffTP1−Hose $A$*HoseTF1−Hose $B$*HoseATF1$^2$ and

TrueDiffTP2=DiffTP2−Hose $A$*HoseTF2−Hose $B$*HoseATF2$^2$, where DiffTP1 is the diffuser flow at a lower pressure for the diffuser and where DiffTP2 is the diffuser flow at a higher pressure for the diffuser.

In this way, the mask pressure can be estimated from known hose characteristics without requiring a pressure transducer in the mask, or directly connected to the mask.

At 410, the apparatus 10 prompts a user for a determination on whether the mask 34 or mask 14 is blocked or not. If the respiratory mask 34 is open, as denoted by 412, the apparatus 10 continues to prompt the user until the user blocks the mask 34, for example, with the flow blocking member 50. If the mask 34 is blocked, as denoted by 414, a first test pressure is applied to the diffuser 36. The mask 34 can be blocked for example, by positioning the flow blocking member 50 adjacent a patient interface of the mask 34, for example.

At 416, the first test pressure, or delivered air flow, is displayed on a display of the CPAP apparatus 10. At 418, the CPAP apparatus prompts a user to determine whether the mask system 14 is leaking. If so, at 420, control proceeds back to 410. If not, control proceeds to 424, at which the flow of the diffuser 36 at a first test pressure is measured and after which, at 426, the CPAP apparatus prompts (actually reminds) the patient or user to keep the mask blocked with the flow blocking member 50. At 428, measurements of diffuser flow of the diffuser 36 at a second test pressure (usually a lower pressure than the first test pressure, but not necessarily lower) and after which, at 430, the CPAP apparatus prompts (actually reminds) the patient or user to keep the mask 34 blocked with the flow blocking member 50. After measuring the diffuser flow at the first and second pressures, the user is prompted to shut off the CPAP apparatus at 432. At 434, processing begins.

During processing, with a processor, for example, the quadratic expression having constants Diff A and Diff B can be used to determine or calculate air flow characteristics of the mask 34. The quadratic expressions are represented as follows:

Diff $A=(zV^2-vZ^2)/(vV^2-Vv^2)$ and

Diff $B=(vZ-zV)/(vV^2-v^2V)$ wherein v is a lower pressure for the diffuser 36, V is an upper pressure for the diffuser, z is a true lower pressure for the diffuser 36 and Z is a true upper pressure for the diffuser 36.

In an alternative embodiment, the background level of the flow generator 12 can be measured to characterize background noise during testing of the diffuser. The background level can be subtracted from a raw snore signal to derive a true snore level on the CPAP apparatus 10 and other flow generators that measure snore. This procedure could be used to calibrate the snore scale factor in the case where the flow blocking member 50 includes some type of snore source to perform in this manner. In accordance with the measurements shown in FIG. 5, the test pressure or flow is held substantially constant for about 10 to about 20 seconds with mean flows and pressures being recorded during this time period.

During this operation, the mask system 14 is pressurized at the highest test pressure to expose any leaks. This can be checked by observing the displayed flow on the display, for example, and adjusting the flow blocking member 50 so that the displayed flow remains substantially constant and at a minimum.

During the operation and implementation of the above described method, there are a number of consistency checks that can be done at 436 to check whether the characterization of the mask is correct. If characterization is correct, then the method ends. If the characterization is not correct for some reason, the method starts over, at 400, but if the characterization is correct, then the method ends at 440.

Described below is one hypothetical example to further illustrate the principles of the method described in FIG. 4. The results of which are shown in Table 3.

For a test flow of 40 L/min, for example, a pressure drop=HoseA*F+HoseB*$F^2$=0.75 cm $H_2O$. If a hypothetical mask system has a diffuser leak that has a flow of 50 L/min at a mask pressure of 20 cm $H_2O$, and that 10 cm $H_2O$ of this is the linear component, the two diffuser constants would be DiffA=0.2 and DiffB=4*$10^3$. At a test flow of 20 L/min, the test pressure (at the mask) will be 5.6 cm $H_2O$.

To calculate the hose pressure drop for the diffuser test flows, the following formula is used: HoseDrop=HoseA*F+ HoseB*$F^2$. At a flow of 20 L/min, the hose pressure drop=0.3125 cm $H_2O$ and the diffuser test pressure (at the flow generator)=5.9125 cm $H_2O$. At a flow of 50 L/min, however, the hose pressure drop=1.015652 cm $H_2O$ and the diffuser test pressure (at the flow generator)=21.01562 cm $H_2O$.

Table 3, as shown below, summarizes the results for our example.

TABLE 3

| Parameter | Test value | Result | Test Value |
|---|---|---|---|
| Hose test flow 1 | 40 L/min | Test pressure for this | 0.75 cm$H_2O$ |
| Hose test flow 2 | 80 L/min | Test pressure for this | 2 cm$H_2O$ |
| Diffuser test pressure 1 | 5.9125 cm$H_2O$ | Diffuser flow at this pressure | 20 L/min |
| Diffuser test.pressure 2 | 21.0125 cm$H_2O$ | Diffuser flow at this pressure | 50 L/min |

| Derived results: | | | |
|---|---|---|---|
| HoseA | HoseB | DiffA | DiffB |
| 0.0125 | 11.5625 * $10^{-4}$ | 0.2 | 4 * $10^{-3}$ |

The square law non linearity in the pressure and flow sensors described above will have a minimal effect on this system, as these are added to the square law characteristics of the mask system, and so will tend to be automatically calibrated into the method described in FIG. 4. Further, errors in the zero point of the flow and pressure sensors are accounted for during the method described in FIG. 4. The functions shown and described above in accordance with the principles of the invention can be executed in any type of programming language. An example of fragments of generic source code is shown in the attached APPENDIX. The fragments of generic source code are shown in a generic computing language, such as, for example, C++, but may be implemented in other generic programming languages or programs as well.

In another form of the invention, apparatus is provided including a blower or flow generator, the blower including a pressure and flow sensor, the apparatus including a display for prompting a user and a mask blocking tool. The apparatus is programmed to perform the series of steps shown in Table 4. Table 4 shows what the flow generator does during each step, what the user is prompted to do and how the user should respond to the prompt. In the first step, the system is zeroed. Steps 2 and 3 constitute the part of the sequence where the hose characteristics are measured. In steps 4 and 5, the user is prompted to block the mask and the blocking is subsequently verified. In steps 6 and 7 the diffuser characteristics are measured whilst the mask is blocked. Finally in steps 8 and 9, the data collected during the previous steps is processed to determine the conduit characteristics and the diffuser characteristics. Also, in step 9, the data and results are checked for consistency.

TABLE 4

| Step | Flow Generator does | Prompt | User response |
|---|---|---|---|
| 1 | Zero of pressure and flow sensors | Ensure that mask is connected to flow generator and not patient | Set up mask system as required Press key when ready |
| 2 | Measure hose pressure drop at test flow 1 (~40 L/min) | Measuring hose characteristics | Wait |
| 3 | Measure hose pressure drop at test flow 2 (~80 L/min) | Measuring hose characteristics | Wait |
| 4 | Ask operator to block mask | Block mask with the mask blocking tool | Press key when done |
| 5 | Test for properly blocked mask: Apply diffuser test. pressure 2 (~12 cm$H_2O$) and display delivered flow | Check that the mask is not leaking and that display flow is minimum | Press key when done |

TABLE 4-continued

| Step | Flow Generator does | Prompt | User response |
|---|---|---|---|
| 6 | Measure diffuser at test pressure 2 (~12 cm$H_2O$) | Testing diffuser, Hold mask blocked | Wait |
| 7 | Measure diffuser at test pressure 1 (~6 cm$H_2O$) | Testing diffuser, Hold mask blocked | Wait |
| 8 | Turn off flow generator | Finished, remove mask from blocking tool | Remove tool and wait |
| 9 | Do mask characterisation and check for consistency | Report any errors | Accept characterisation or return to step I |

Notes:
1. For all measurements, the test pressure or flow should be held steady for 10 to seconds with mean flows and pressures recorded during this time.
2. The measured pressures during steps 2 and 3 can be very low (0.2 to 2 cm$H_2O$). This may entail accurate and steady control of the fan at unusually low (for CPAP) pressures. The ideal mode of control is constant flow delivery.
3. In step 5, a good leak proof seal is provided using the blocking tool. During this step, the mask is pressurised at the highest test pressure to expose any leaks. This can be checked by observing the displayed flow and adjusting the blocking tool so this is steady and minimum.
4. There are a number of consistency checks that can be done in step 8 to check the characterisation. Some of these are:
Check on bounds of the test pressures and flow.
Check on expected values for the A and B factors for the hose drop and diffuser leak models.
Check that none of the A and B factors are negative (the pressure flow curves must have an increasing gradient).

In a pressure delivery apparatus, control of treatment of the patient typically requires that certain prescribed levels of pressure be delivered to the patient's airway. However, when the pressure is measured away from the mask such as in or near the flow generator 12, the flow characteristics of the airway circuit (air delivery hose 16 and mask system 14) between the pressure sensor 44 and the patient's airway will cause the remotely taken pressure measurement to be different from the actual pressure at the contact point between the mask system 14 and the patient's airway. To accommodate different or changing hose and mask systems that may be used by a patient, some of the foregoing principles may be implemented in a learn or test mode that can be automated to determine the flow characteristics of the connected airway circuit.

With such a device, a pressure drop (delta p) can be determined from the learned flow characteristics of the airway circuit before it is used by the patient. As there are many possible configurations for the airway circuit, each with a different impedance or resistance to flow, the learn mode provides the user with an easy alternative to the error prone entering of large amounts of configuration data that would otherwise be required.

Thus, when the pressure is measured by the pressure sensor 44 at a remote location in the airway circuit during treatment, such as near the flow generator 14, the apparatus can dynamically determine the pressure drop from the previously learned characteristics of the airway circuit so that the pressure delivery apparatus can assess or estimate the actual pressure that is being delivered to the patient at the patient interface during treatment. In the preferred embodiment, the learned characteristic of the airway circuit is the pneumatic impedance (resistance to flow) which can be used to determine the specific pressure drop associated with any particular level of flow measured by the apparatus during treatment.

Figure 6:
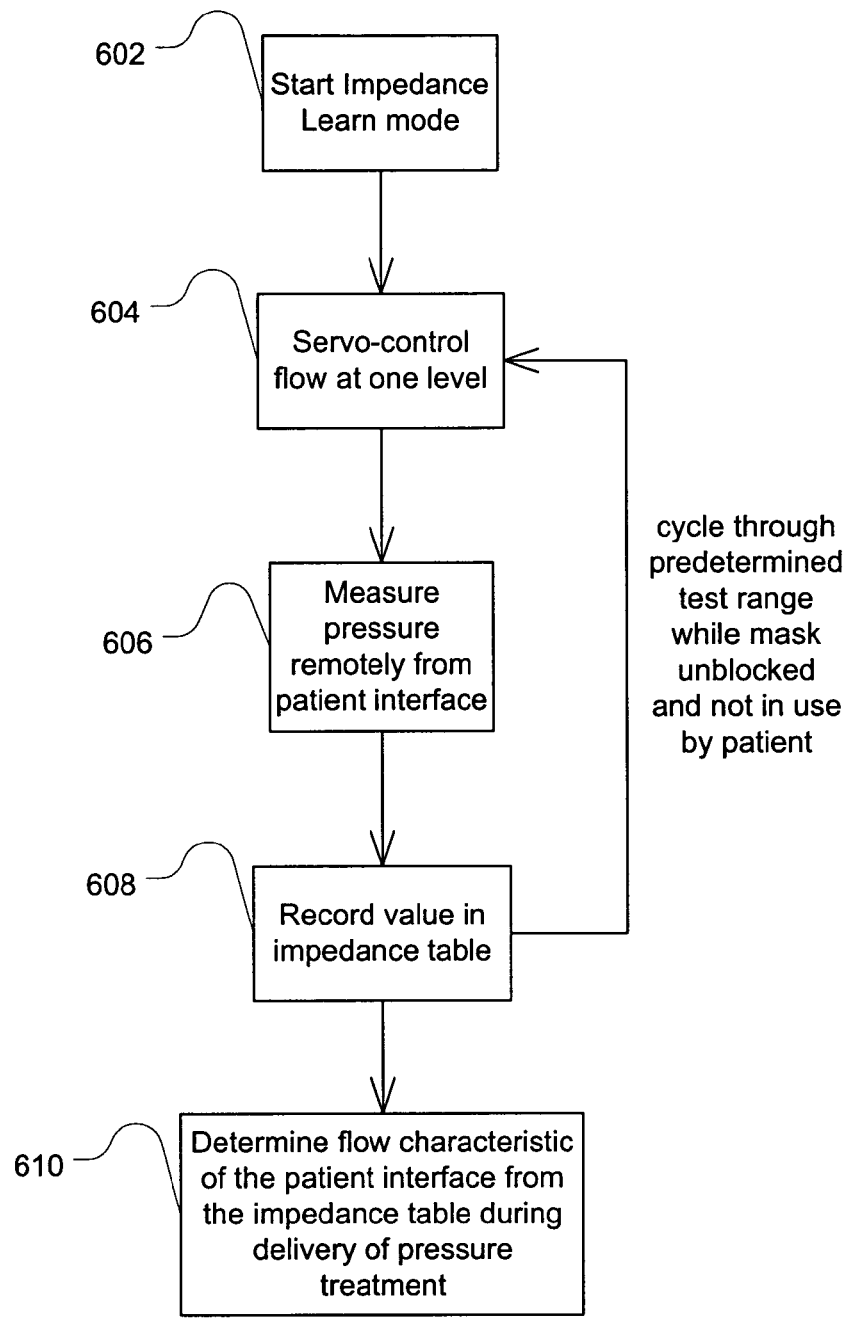
FIG. 6 is a flow chart illustrating steps in an embodiment of an impedence learn mode of the invention.

Steps from such a methodology of the apparatus are illustrated in the flow chart of FIG. 6. In step 602, the learn mode is started. The learn mode may be initiated automatically when the pressure delivery apparatus is turned on or a user may initiate the mode. The apparatus may also initiate the mode or prompt the user to initiate the mode when it detects that the airway circuit has been disconnected and reconnected from the device, for example, by a pressure switch located at the physical connection point between the airway circuit and the pressure delivery apparatus or flow generator.

Figure 7:
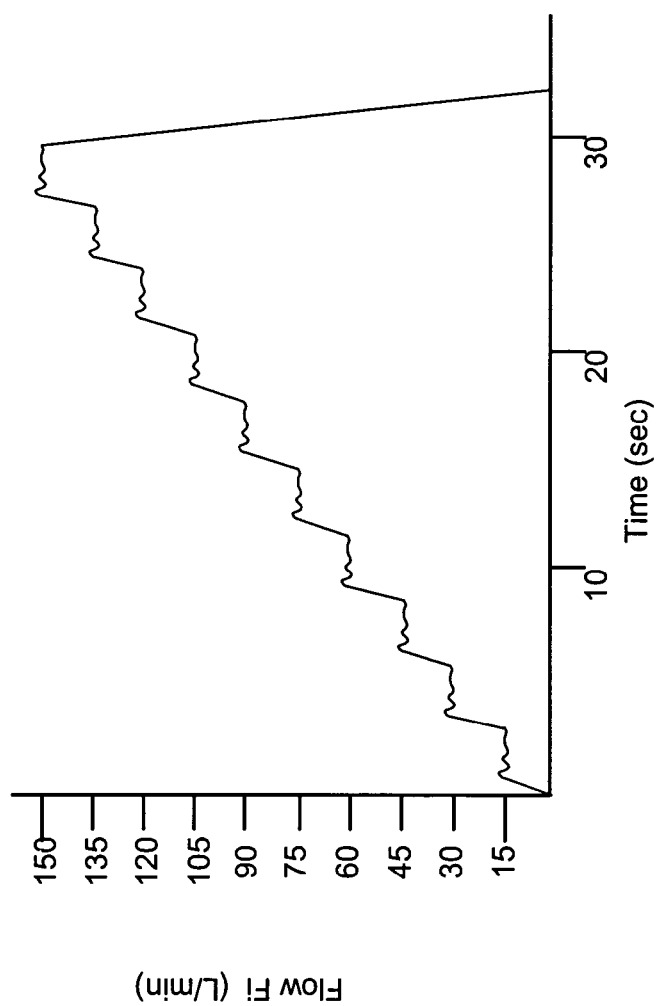
FIG. 7 is a flow verses time graph illustrating a preferred impedance learn mode.

In step 604, the flow generator 14 is set or servo-controlled to deliver a particular flow value $F_i$. Once the flow generator stabilizes briefly at this particular flow level to ensure that an accurate pressure measurement may be taken, the pressure $P_i$ is measured in step 606. The pressure $P_i$ associated with the particular flow value $F_i$ is then recorded in an impedance table in step 608. These steps (604, 606 and 608) are repeated for a range of flow values ($F_i$ for i=1 to n) to record a plurality of pressure values P. In the preferred embodiment, the flow generator 14 is controlled to deliver a range of flows from about 15 L/min and increasing to about 150 L/min, recording each pressure at about 15 L/min intervals (n=10). Such an automated process can take approximately 30 seconds to complete. The performance of an apparatus executing a preferred learn mode is illustrated in the flow verses time curve of FIG. 7.

Of course, the intervals that separate the measurements may be reduced or increased as desired and the range of flows may be adjusted as needed. Such a process may even generate a substantially continuous impedance curve into the look up table with an interval of 1 L/min or less. However, as will be more fully described below, the 15 L/min interval is preferably chosen to decrease the time of the impedance learn mode, to reduce the size of the memory table in which the measured points are stored and to minimize error associated with determining impedance between the actual measurements.

As those skilled in the art will recognize, in the cycling process, although it is preferred that the flow is controlled and pressure measured, as an alternative pressure may be controlled and each associated flow value measured and the table can be populated accordingly.

During the measurement cycling it is desired that the patient interface remain in an unblocked state permitting the flow from the flow generator to escape from the mask freely. Thus, the mask will not be worn on the face of the patient in a manner that would apply pressure to the patient's airway during the learn operation. As those skilled in the art will recognize, this unblocked state of the mask will effectively mean that the pressure at the mask portion is approximately 0 or ambient. Thus, the recorded pressure values $P_i$ taken away from the mask effectively represents the pressure drop associated with the airway circuit from the location of the measured pressure through the mask since $P_{drop}=P_{blower}-P_{mask}$. Accordingly, during the learn mode, the apparatus will warn the user to remove the mask with an alarm or other prompting on a display of the apparatus before and/or during the learn mode operation. Optionally, it will check to confirm that the mask is not being used during the operation as described in more detail later herein.

The result of these repeated operations is a table of pressure values (pressure drop) that may be indexed by a flow value in step 610 during the provision of pressure treatment. Thus, for any particular flow that may be measured during the delivery of pressure treatment to a patient, the flow can serve as an index to access the impedance table to determine the associated pressure drop by a lookup operation. Thus, the pressure measurements are preferably stored in a table. However, those skilled in the art will recognize other ways of storing and accessing the impedance data for later use. For example, the flow values need not necessarily be recorded in the table since the flow associated with the locations in the table may be determined in relation to its location according to a formula by which the pressure measurements were taken in the cycling process (i.e., the associated flow for the pressure measurement at location n={(interval L/min*(n−1))+start pressure}; e.g., flow at n={(15 L/min*(n−1))+15 L/min}) With the table of impedance data and the remotely measured pressure, for example, at the blower, an estimated pressure at the mask can be determined by the following equation: $P_{mask}=P_{blower}-P_{drop}$. Similarly, a target pressure for the mask $P_{masktarget}$ can be servo-controlled at the flow generator by adjusting for the $P_{drop}$ as follows: $P_{error}=P_{masktarket}-P_{blower}+P_{drop}$.

As previously discussed, in the preferred embodiment, the automated learn mode measures pressure $P_i$ at certain measurement intervals over the selected range of flows. This process will leave certain gaps in the impedance table for flow values falling within the interval. To overcome this issue, an interpolation operation is performed to derive additional impedance data between measured points. This interpolation procedure may be performed at the completion of the measurement cycle to derive further data which may be stored in the look-up table depending on the memory size of the data storage medium. However, interpolation may be performed dynamically during treatment of a patient on an as-needed basis when impedance data is needed for a flow value that cannot be indexed into the look up table because that flow value is not in the table and it has no associated pressure measurement in the table.

Figure 8:
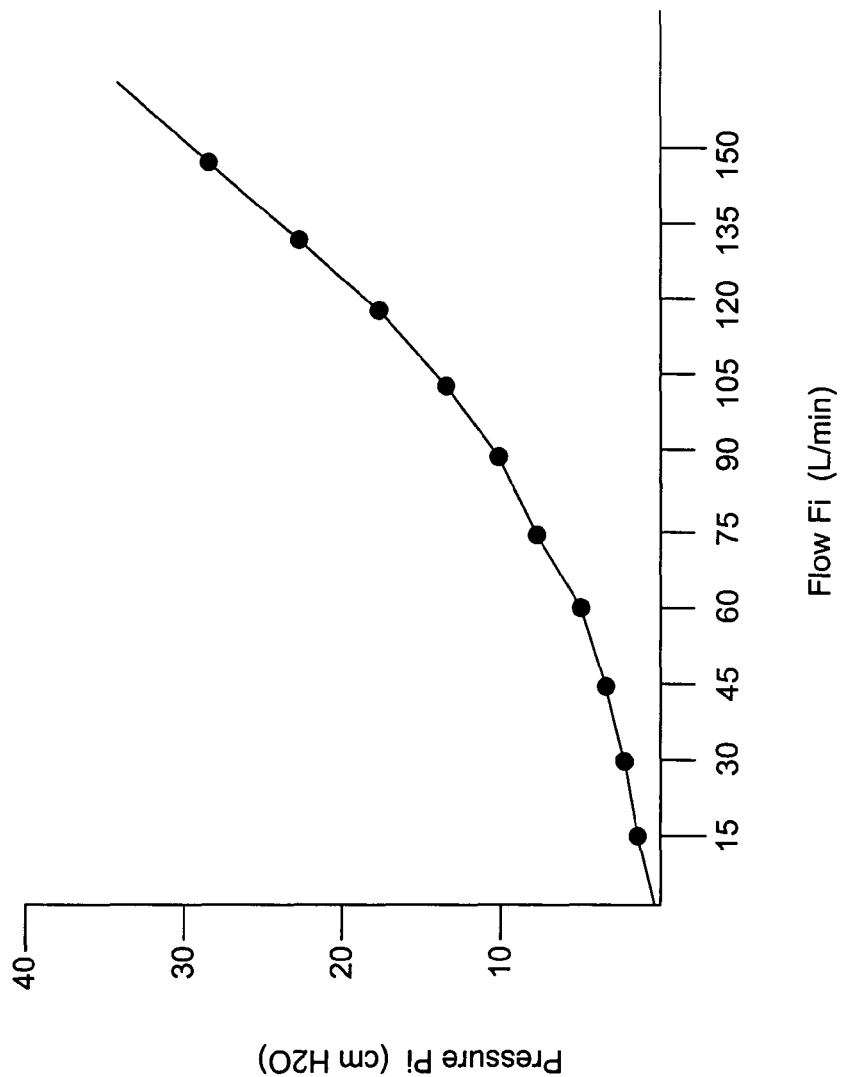
FIG. 8 is a graph illustrating impedance data derived in an impedance learn mode of the invention.

In the preferred embodiment, interpolation is performed linearly between measured data points. FIG. 8 illustrates a graph of hypothetical impedance data from a learning routine in which linear interpolation is depicted between measured data points. Due to the use of linear interpolation, the interval between measurements, which relates to the number of data points stored in the table, is chosen to minimize errors since interpolation of impedance in the table can introduce errors as well as minimize data storage. The use of more measurements with a smaller measurement interval will result in a longer learn mode operation and the need for more storage but it will increase the accuracy of the interpolation between points. This tradeoff between time, size and accuracy is resolved in the following analysis.

If it is assumed that the impedance is a quadratic of the form $ax^2+bx+c$ then the error introduced by using linear interpolation of interval spacing d can be calculated as the difference between the two at the midpoint of the interpolation. Using a two-point formula this can be calculated as Error(d)=$(ad^2)/4$. In other words, the error is dependent only on the square of the distance between the points used for interpolation. To find a desired spacing between measured data, a d is found such that Error(d) is less than some small error such as about 0.05 cm. By comparison between a fully measured impedance curve and several chosen curves generated by linear interpolation from points on the measured curve, the Error(d) formula can be utilized to calculate a d to yield an interval that will result in an acceptable error.

Of course, as an alternative, the recorded values may be used to derive a quadratic equation for impedance for the airway circuit which can then be used with or without the lookup table to calculate the pressure drop based on any determined flow. Such an equation may even be used to further populate the lookup table with additional data within and beyond the flow range of the pressure measuring routine, for example, pressure values associated with flows in a range from 150 L/min to 300 L/min. Of course, these higher values if needed may also be projected by a simple linear interpolation from neighboring data points and determined with or without storing them in a look up table.

The use of a linearly interpolated look up table is desirable relative to using a polynomial for several reasons including:
1. Implementation efficiency—a look up table is computationally more efficient;
2. Accuracy—although a quadratic can be found that will fit all known circuit impedances well, slight errors in the coefficients due to fixed point round off will introduce errors that exceed those achievable with a look up table.
3. Ease of implementation—as the values used in the lookup table are those actually measured the implementation is straightforward.
4. Less prone to errors with unknown airway circuit components. It is possible that some airway circuit components, such as AB filters, could be added at a later date that do not have a standard quadratic characteristic. A look up table will be able to cope with these irregularities.

To ensure that an accurate impedance table is derived in the automated impedance learn mode, several safety procedures may be implemented. For example, a pressure sensing tube with a known impedance or pressure drop may be optionally connected to the mask system 14 for the learning operation to confirm that the mask pressure remains near or at zero. With such a sensing tube and a remotely located pressure sensor, during the cycling of flow and the taking of pressure measurements of step 606 or any other time before use of the impedance data, if it is determined that the mask pressure exceeds a threshold value, such as about 3 or 5 cm $H_2O$, the procedure can be aborted, that is, the learn mode process may be stopped and/or the determined values may be ignored or disregarded. Similarly, the apparatus can check to ascertain whether any determined pressure drop exceeds by a threshold value, for example, about 3 cm $H_2O$, a predetermined upper pressure drop limit for any particular airway circuit. For example, if a particular mask system has a pressure limit of 17 cm $H_2O$ and if a pressure drop determined in the learn mode exceeds this by 3 cm $H_2O$, use of the current learn mode data can be aborted. The apparatus may also abort the learn mode operation if any predetermined flow level in the test range can not be generated through the airway circuit. If any of these safety tests result in aborting the learn procedure, the apparatus will reset to a previously known look up table derived from a successful learn mode. Optionally, the entries in the table may default to a safe value (such as for example zero) to indicate no pressure drop or impedance so that the pressure delivery apparatus will not compensate for an airway circuit pressure drop at any flow. Thus, if an error occurs during the learn mode or if the procedure is aborted, the table may be used in setting the pressure but the impedance of the hose and mask will not be accounted for.

The foregoing presentation of the described embodiments is provided to enable any person skilled in the art to make or use the present invention. Various modifications to these embodiments are possible, and the generic principles presented herein may be applied to other embodiments as well. For example, the invention may be implemented in part or in whole as analog or digital circuitry, as a hard-wired circuit, as a circuit configuration fabricated into an application-specific integrated circuit, or as a firmware program loaded into non-volatile storage or a software program loaded from or into a data storage medium as machine-readable code, such code being instructions executable by an array of logic elements such as a microprocessor or other digital signal processing unit.

In another example, apparatus and methods in accordance with the invention may use predetermined characteristics of the conduit in order to determine the characteristics of the diffuser. In this way, instead of a characterisation procedure using two steps namely a first part in which the mask is not blocked and a second part in which the mask is blocked, a characterisation procedure may only require the second step, the first step already having been done at an earlier stage. Hence if a technician or physician were to carry out one complete characterisation, that is both conduit and mask diffuser, and then at a later stage only change the mask and diffuser, it would not be necessary to recharacterise the conduit. Alternatively, if the apparatus were to be used with a conduit whose character was already known and stored in the apparatus (for example, having been determined in a factory test), only the second step of the procedure would be necessary.

Thus, the present invention is not intended to be limited to the embodiments shown above but rather is to be accorded the widest scope consistent with the principles and novel features disclosed in any fashion herein.

The invention claimed is:

1. A method for determining a characteristic of a mask system connected to a ventilation delivery device for delivering breathable air to a patient, where said ventilation delivery device includes a processor-controlled blower, a pressure sensor, and a flow sensor; and said mask system includes a patient interface with a diffuser and an air delivery hose, the method comprising the steps of:

delivering breathable air at a first flow rate and measuring a corresponding first pressure drop in the air delivery hose, delivering breathable air at a second flow rate and measuring a corresponding second pressure drop in the air delivery hose, blocking the patient interface, applying a first test pressure to the diffuser, minimizing unintentional leak and measuring a first diffuser flow corresponding to the first test pressure, applying a second test pressure to the diffuser and measuring a corresponding second diffuser flow, and determining a characteristic of the mask system as a function of the first and the second flow rates and their corresponding measured pressure drops, and the first and the second test pressures and their corresponding measured diffuser flows.

2. The method of claim 1 wherein the function includes a quadratic.

3. The method of claim 1 wherein the characteristic is flow.

4. The method of claim 1 wherein the characteristic is patient interface pressure.

5. The method of claim 1 wherein the characteristic is pressure drop in the hose.

6. The method of claim 1 wherein the characteristic is diffuser flow.

7. An apparatus for determining a characteristic of a mask system, which includes an air deliver hose and patient interface with a diffuser, connected to a ventilation delivery system including a processor-controlled blower, a pressure sensor, and a flow sensor, wherein said blower is configured to deliver flow at a first constant flow rate, and said pressure sensor is configured to sense a corresponding first pressure drop in the air delivery hose, wherein said blower is configured to subsequently deliver flow at a second constant flow rate, and said pressure sensor is configured to sense a corresponding second pressure drop in the air delivery hose, wherein said patient interface is configured to be blocked, wherein said processor is configured to apply a first test pressure to the diffuser, minimize unintentional leak, and said flow sensor is configured to sense a first diffuser flow corresponding to the first test pressure, wherein said processor is configured to apply a second test pressure to the diffuser, and said flow sensor is configured to sense a corresponding second diffuser flow, and wherein said processor is configured to determine a characteristic of the mask system as a function of the first and the second flow rates and their corresponding measured pressure drops, and the first and the second test pressures and their corresponding measured diffuser flows.

8. The apparatus of claim 7 wherein the function includes a quadratic.

9. The apparatus of claim 7 wherein the characteristic is flow.

10. The apparatus of claim 7 wherein the characteristic is patient interface pressure.

11. The apparatus of claim 7 wherein the characteristic is pressure drop in the hose.

12. The apparatus of claim 7 wherein the characteristic is diffuser flow.

* * * * *